US009278192B2

(12) United States Patent
Copeta et al.

(10) Patent No.: US 9,278,192 B2
(45) Date of Patent: Mar. 8, 2016

(54) RE-ENTRY CATHETERS AND RELATED METHODS

(71) Applicant: Invatec S.p.A., Roncadelle (Bs) (IT)

(72) Inventors: Luca Copeta, Roncadelle (IT); Carlo Guala, Roncadelle (IT); Massimo Morero, Roncadelle (IT); Claudio Silvestro, Roncadelle (IT)

(73) Assignee: Invatec S.p.a., Roncadelle (BS) (IT)

( * ) Notice: Subject to any disclaimer, the term of this patent is extended or adjusted under 35 U.S.C. 154(b) by 400 days.

(21) Appl. No.: 13/764,837

(22) Filed: Feb. 12, 2013

(65) Prior Publication Data

US 2014/0228876 A1 Aug. 14, 2014

(51) Int. Cl.
*A61M 25/01* (2006.01)
*A61B 17/22* (2006.01)
*A61M 25/00* (2006.01)

(52) U.S. Cl.
CPC .. *A61M 25/0194* (2013.01); *A61B 2017/22044* (2013.01); *A61B 2017/22048* (2013.01); *A61B 2017/22071* (2013.01); *A61B 2017/22095* (2013.01); *A61M 2025/0096* (2013.01); *A61M 2025/0197* (2013.01)

(58) Field of Classification Search
CPC ........... A61B 2017/22044; A61B 2017/22048; A61B 2017/22071; A61B 2017/22095; A61B 2025/0096; A61B 2025/0197; A61B 2025/1056; A61M 25/0155; A61M 25/0194
See application file for complete search history.

(56) References Cited

U.S. PATENT DOCUMENTS

| | | | |
|---|---|---|---|
| 5,830,222 A | 11/1998 | Makower |
| 6,068,638 A | 5/2000 | Makower |
| 6,159,225 A | 12/2000 | Makower |
| 6,190,353 B1 | 2/2001 | Makower et al. |
| 6,283,951 B1 | 9/2001 | Flaherty et al. |
| 6,375,615 B1 | 4/2002 | Flaherty et al. |
| 6,508,824 B1 | 1/2003 | Flaherty et al. |
| 6,544,230 B1 | 4/2003 | Flaherty et al. |
| 6,579,311 B1 | 6/2003 | Makower |
| 6,602,241 B2 | 8/2003 | Makower et al. |
| 6,655,386 B1 | 12/2003 | Makower et al. |
| 6,660,024 B1 | 12/2003 | Flaherty et al. |
| 6,685,648 B2 | 2/2004 | Flaherty et al. |
| 6,709,444 B1 | 3/2004 | Makower |
| 6,726,677 B1 | 4/2004 | Flaherty et al. |
| 6,746,464 B1 | 6/2004 | Makower |
| 7,938,819 B2 | 5/2011 | Kugler et al. |
| 8,043,314 B2 | 10/2011 | Noriega et al. |
| 8,083,727 B2 | 12/2011 | Kugler et al. |

(Continued)

FOREIGN PATENT DOCUMENTS

| | | |
|---|---|---|
| WO | WO2007/033052 | 3/2007 |
| WO | WO2008/120209 | 10/2008 |
| WO | WO2010/044816 | 4/2010 |

OTHER PUBLICATIONS

Jaffan A.A., et al., *Balloon Occlusion of Subintimal Tract to Assist Distal Luminal Reentry Into Popliteal Artery*, J Vasc Interv Radiol. Oct. 2012; 23(10):1389-91.

*Primary Examiner* — Adam J Eiseman (57) ABSTRACT

Catheter devices and methods useable for directing a guidewire from a subintimal position within the wall of an artery into the true lumen of that artery or other applications wherein it is desired to direct a guidewire or other elongate device from one location to another location within a subject's body.

14 Claims, 10 Drawing Sheets

(56) References Cited

U.S. PATENT DOCUMENTS

| | | |
|---|---|---|
| 8,257,382 B2 | 9/2012 | Rottenberg et al. |
| 8,323,261 B2 | 12/2012 | Kugler et al. |
| 8,353,922 B2 | 1/2013 | Noriega et al. |
| 2001/0034547 A1* | 10/2001 | Hall et al. .................... 623/1.11 |
| 2011/0144677 A1 | 6/2011 | Ward et al. |
| 2013/0072957 A1* | 3/2013 | Anderson ..................... 606/194 |
| 2014/0018837 A1* | 1/2014 | Zhou et al. .................... 606/194 |
| 2014/0194776 A1* | 7/2014 | Gunday et al. ................ 600/567 |

* cited by examiner

RE-ENTRY CATHETERS AND RELATED METHODS

FIELD OF THE INVENTION

The present invention relates generally to the fields of mechanical engineering and medicine and more particularly to apparatus and methods for directing the advancement of catheters and other elongate medical devices.

BACKGROUND

There are numerous medical procedures in which it is desirable to re-direct a guidewire or other elongate medical device from one location to another location within the body of a human or non-human animal subject. For example, during endovascular treatment of total or near-total occlusions in arteries, a guidewire may sometimes become embedded within the wall of an artery and it then becomes desirable to re-direct the distal end of that guidewire from its position within the artery wall into the true lumen of the artery.

Chronic total occlusions (CTOs) of arteries can occur in coronary as well as peripheral arteries. It has been estimated that approximately 10% of all endovascular angioplasty procedures are currently undertaken to treat CTOs. The factor that is most determinative of whether a CTO can be successfully treated by endovascular angioplasty is the ability (or inability) to initially pass a guidewire from a position within the true lumen of the artery proximal to the CTO, through or around the CTO and then into the true lumen of the artery at a location distal to the CTO. If a guidewire can be placed in this manner, it is typically possible to then perform angioplasty and stenting over that pre-placed guidewire to successfully restore blood flow through or around the CTO.

In CTOs where the occlusive matter is soft (or where the occlusion is less than total) a guidewire can simply be pushed through the occlusive matter itself, thereby achieving the desired placement of the guidewire with the guidewire remaining within the true lumen of the artery. However, in other cases, such as where the artery is totally occluded by hard, calcified atherosclerotic plaque, the guidewire may tend to deviate to one side, causing the distal end of the guidewire to penetrate into the wall of the artery. When this occurs, the guidewire may be pushed past the obstruction while still within the artery wall. This creates a "subintimal tract" within the wall. In many cases, the guidewire may be advanced sufficiently to extend the subintimal tract past the obstruction. However, in these cases where the guidewire has been successfully been advanced past the obstruction, the distal end of the guidewire typically remains entrapped within the newly-created subintimal tract. It then becomes necessary to re-direct the distal end of the guidewire from its entrapped location within the subintimal tract into the true lumen of the artery at a location distal to the obstruction. Following successful re-entry of the guidewire into the true lumen, balloon dilation and stenting of the subintimal tract may be accomplished to create a suitable channel for antegrade arterial blood flow around the obstruction.

The prior art has included a number of true lumen re-entry devices that are potentially useable to redirect a subintimally entrapped guidewire into the true lumen of the artery. Commercial examples of such re-entry devices include the Pioneer® Catheter (Medtronic Vascular, Santa Rosa, Calif.); the OUTBACK® LTD® Re-Entry Catheter (Cordis Corporation, Miami, Fla.) and the Enteer™ Re-entry System (Covidien/eV3, Plymouth, Minn.). Other examples are described in U.S. Pat. No. 5,830,222 (Makower); U.S. Pat. No. 6,068,638 (Makower); U.S. Pat. No. 6,159,225 (Makower); U.S. Pat. No. 6,190,353 (Makower, et al.); U.S. Pat. No. 6,283,951 (Flaherty, et al.); U.S. Pat. No. 6,375,615 (Flaherty, et al.); U.S. Pat. No. 6,508,824 (Flaherty, et al.); U.S. Pat. No. 6,544,230 (Flaherty, et al.); U.S. Pat. No. 6,655,386 (Makower et al.); U.S. Pat. No. 6,579,311 (Makower); U.S. Pat. No. 6,602,241 (Makower, et al.); U.S. Pat. No. 6,655,386 (Makower, et al.); U.S. Pat. No. 6,660,024 (Flaherty, et al.); U.S. Pat. No. 6,685,648 (Flaherty, et al.); U.S. Pat. No. 6,709,444 (Makower); U.S. Pat. No. 6,726,677 (Flaherty, et al.); U.S. Pat. No. 6,746,464 (Makower); U.S. Pat. No. 8,323,261 (Kugler, et al.); U.S. Pat. No. 8,083,727 (Kugler, et al.); U.S. Pat. No. 7,938,819 (Kugler, et al.); U.S. Pat. No. 8,257,382 (Rottenberg, et al.); U.S. Pat. No. 8,353,922 (Noriega, et al.); U.S. Pat. No. 8,043,314 (Noriega, et al.)

A recent published report describes the use of a balloon occlusion technique for diverting a guidewire from a subintimal tract into the true lumen of an artery, in lieu of using a re-entry catheter. In this reported case, a 0.035 inch guidewire was initially used to form the subintimal tract that extended past an obstructive lesion. That 0.035 inch guidewire was then removed and a separate 0.018 inch guidewire was selectively advanced into the subintimal tract. A low-profile balloon catheter was then advanced over the 0.018 inch wire into the subintimal tract. The balloon was inflated to block the subintimal tract. A 0.035 inch guidewire was then advanced through the subintimal tract next to the balloon catheter. The presence of inflated balloon within the subintimal tract caused the advancing 0.035 inch guidewire to divert out of the initial subintimal tract and into the true lumen of the artery, distal to the obstruction. Although this procedure did successfully cause the 0.035 inch guidewire to re-enter the true lumen of the artery without use of a separate re-entry catheter, this procedure did involve several time consuming steps and required the use of several guidewires as well as a separate balloon catheter. Additionally, as the authors note, this procedure must be performed with caution as advancement of the 0.035 inch guidewire past the inflated balloon could result in inadvertent perforation of the artery with resultant hematoma or arteriovenous fistula formation. Jaffan A. A., et al., *Balloon Occlusion Of Subintimal Tract To Assist Distal Luminal Reentry Into Popliteal Artery*, J Vasc Intery Radiol. 2012 October; 23(10):1389-91.

There remains a need in the art for the development of different and improved devices and methods useable for redirecting a subintimally entrapped guidewire back into the true lumen of an artery in a safe and efficient manner.

SUMMARY OF THE INVENTION

The present invention provides catheter devices and methods useable for directing a guidewire from a subintimal position within the wall of an artery into the true lumen of that artery or other applications wherein it is desired to direct a guidewire or other elongate device from one location to another location within a subject's body.

In accordance with one aspect of the invention, there is provided a guidewire directing device (i.e., a true lumen re-entry device) that comprises an elongate shaft having a distal portion with a distal end and a lumen that extends to a distal outlet opening. An expandable member (e.g., a balloon or expandable cage) is positioned on the distal portion of the elongate shaft. At least one navigation apparatus is also positioned on the distal portion of the elongate shaft. Proximal end(s) of the navigation apparatus is/are attached to the device shaft while distal end(s) of the navigation apparatus are unattached to the elongate shaft. The device is transitionable between a) a first configuration wherein the expandable member is non-expanded and the distal portion of the elongate shaft is substantially straight and b) a second configuration wherein the expandable member is expanded, thereby causing the expandable member to displace to one side of the navigation apparatus, which in turn results in lateral curvature of the distal portion of the elongate shaft. This device is advanceable, while in its first configuration, over a guidewire whose distal end is subintimally entrapped within an artery wall. With the guidewire retracted into the lumen of the device, the expandable member is expanded, causing the device to transition from its first configuration to its second configuration while situated within the subintimal space. This causes the expandable member to displace inwardly toward the true lumen rather than outwardly toward the muscular sheath of the artery, as this is the path of least resistance to its expansion. As this occurs, the distal portion of the elongate shaft curves toward the true lumen of the artery such that the distal opening of the device lumen is aimed or directed toward the artery's true lumen. The guidewire (or alternatively some other elongate device such as a probe, needle, stylet, penetrator, etc) is then advanced out of the distal opening of the device and into the true lumen of the artery. The device may then be returned to its first configuration and removed from the body, leaving the guidewire in place. Other devices (e.g., balloon catheters, stents, etc.) may then be delivered over the guidewire and used to establish a blood flow channel around the arterial obstruction.

Further in accordance with the present invention there are provided methods for causing a guidewire that has become entrapped in a subintimal tract within a blood vessel wall to re-enter the true lumen of the blood vessel without requiring the use of additional guidewire(s).

Still further aspects, details and embodiments of the present invention will be understood by those of skill in the art upon reading the following detailed description of the invention and the accompanying drawings.

DETAILED DESCRIPTION

Figures 1, 1C, 1D, 1E:
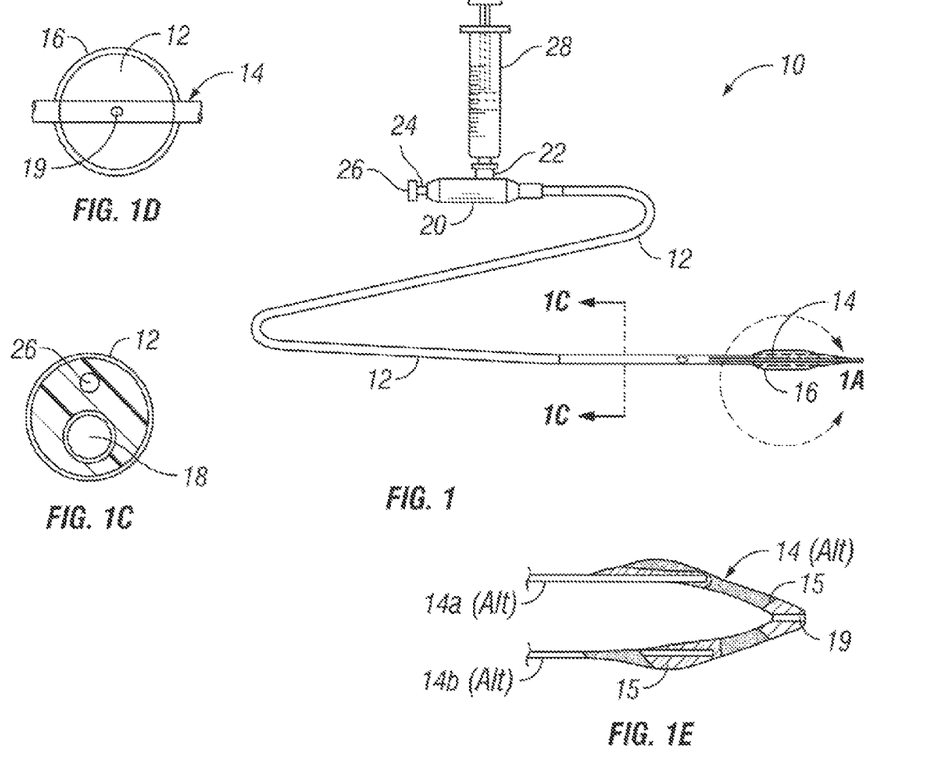
FIG. 1 is a side view of one embodiment of a re-entry catheter of the present invention.
FIG. 1C is a transverse sectional view through line 1C-1C of FIG. 1.
FIG. 1D is an end view of the device of FIG. 1.
FIG. 1E is a top view of a distal end portion of an alternative construction of the device of FIG. 1.

FIGS. 1 through 1E generally show one embodiment of a re-entry catheter device 10 of the present invention. This re-entry catheter device 10 generally comprises a flexible elongate shaft 12, a navigation apparatus 14 and balloon 16 positioned on a distal portion of the elongate shaft 12 and a proximal hub 20 on the proximal end of the elongate shaft 12. Preferably, balloon 16 is a compliant balloon. A guidewire lumen 18 extends through the elongate shaft 12 and terminates distally in an opening at the distal end DE of the shaft 12. A balloon inflation lumen 26 also extends through the shaft 12 to facilitate inflation and deflation of the balloon 16. The proximal hub 20 has a proximal port 24 which communicates with the guidewire lumen 18 and a balloon inflation port 22 which communicates with the balloon inflation lumen 26.

In the particular embodiment of FIGS. 1 through 1E, the navigation apparatus 14 generally comprises a loop shaped (e.g., U shaped) structure which comprises a right side portion 14a, a left side portion 14b and an open area 14c. The proximal ends of the right and left side portions 14a, 14b are separate and attached to opposite sides of the elongate shaft, proximal to balloon 16. The distal ends of the right and left side portions 14a, 14b are conjoined or commonly connected to a unitary distal end member that forms the distal end of the navigation apparatus 14. The distal end of the navigation apparatus 14 is free floating and unattached to the elongate shaft 12. A guidewire passage aperture 19 extends axially through the distal end of the navigation apparatus 14, as shown.

The navigation apparatus 14 may be formed of any suitable material(s) such as metal and/or plastic. In some embodiments, all of part of the navigation apparatus 14 may be formed of superelastic nickel-titanium (i.e., Nitinol). In this regard, the navigation apparatus may be formed of wire or other elongate material (e.g., strips or ribbons). Or, in some embodiments, it may be cut from a nickel-titanium tube, as will be discussed in more detail herebelow in relation to FIGS. 7 through 8B.

Also, the navigation apparatus 14 may be of one-piece construction formed from a single component (e.g., a single wire, tube, ribbon, etc.) or it may be fabricated or constructed from more than one component. One example of multiple component construction is shown in FIG. 1E, wherein the navigation apparatus 14(alt) comprises right and left metal side portions 14a(alt), 14b(alt) which are molded, fused or affixed to a polymer end member 15 having the guidewire passage aperture 19 formed therein. This polymer end member 15 may be injection molded or otherwise formed to any desired shape. For example, this end member 15 may have a blunt pointed tip designed to effect atraumatic blunt tissue separation as it advances through a subintimal tract within an artery wall.

The balloon 16 may be of any any suitable type or formed of any suitable type of material. In the particular example shown in the drawings, the balloon 16 comprises a compliant balloon.

Figure 1A:
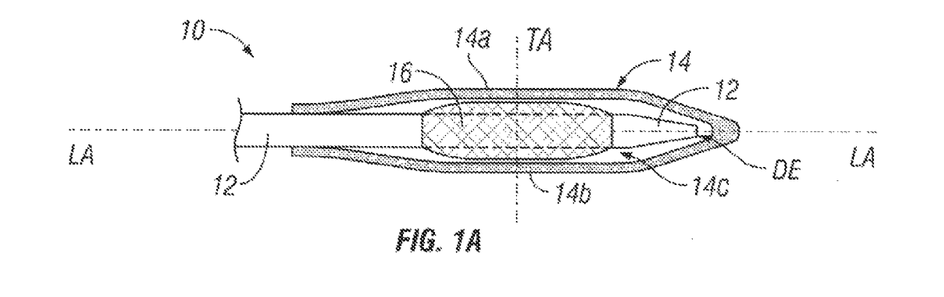
FIG. 1A is a top view of portion 1A of FIG. 1.

As shown in conjunction with the top view of FIG. 1A, a longitudinal axis LA and a transverse axis TA are projectable through the navigation member 14.

Figure 1B:
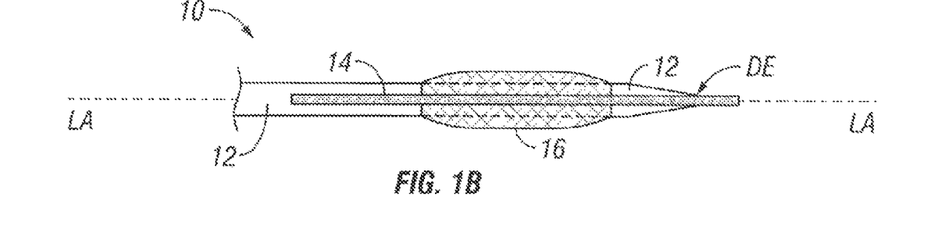
FIG. 1B is a side top view of portion 1A of FIG. 1.

As seen in FIGS. 1A and 1B, when this device 10 is in its first configuration, the balloon 16 is deflated and the distal portion of the elongate shaft 12 extends straight within the open area 14c of the navigation apparatus 14 such that the open distal end DE of the elongate shaft 12 is slightly proximal to, and may be aligned with, the guidewire passage aperture 19 located in the distal end of the navigation apparatus 14. This allows the device 10 to be advanced over a subintimally entrapped guidewire. The guidewire passage aperture 19 helps in stabilizing the navigation of apparatus 14. The navigation apparatus 14 is coupled to the guidewire by passage of the guidewire through aperture 19, thereby keeping the navigation apparatus 14 substantially parallel to the guidewire and deterring inadvertent lateral movement of the navigation apparatus 14 as the device 10 is advanced over the guidewire along the subintimal tract When it is desired to transition the device 10 to its second configuration, the balloon 16 is inflated. As the balloon 16 expands, its width becomes wider than the width of the open area 14c within the navigation apparatus 14. This causes the balloon to selectively bulge either above or below the open area 14c. Typically, this selective bulging of the balloon will be in whichever direction presents the least resistance to its expansion. For example, if body tissue located immediately below the open area 14c is less elastic or less compressible than body tissue located immediately above the open area 14c, the balloon 16 will selectively bulge below the open area 14c. This causes concurrent curvature of the distal portion of the elongate shaft 12 in the same direction.

To appreciate the advantageous uses of the above-described re-entry catheter device 10, it is helpful to understand the disorders it is useable to treat. In many cases, the device 10 may be used to treat a CTO in an artery of the leg which has resulted from uncontrolled Peripheral Arterial Disease (PAD). PAD in a lower limb can cause cramping, intermittent claudication and numbness in the affected leg, especially while walking or during exertion. CTOs in leg arteries are composed of smooth muscle cells, connective tissue, calcium, thrombus, lipids and inflammatory cells. These lesions may be more than 20 cm in length. Often they are heavily calcified or fibrotic.

Figure 2:
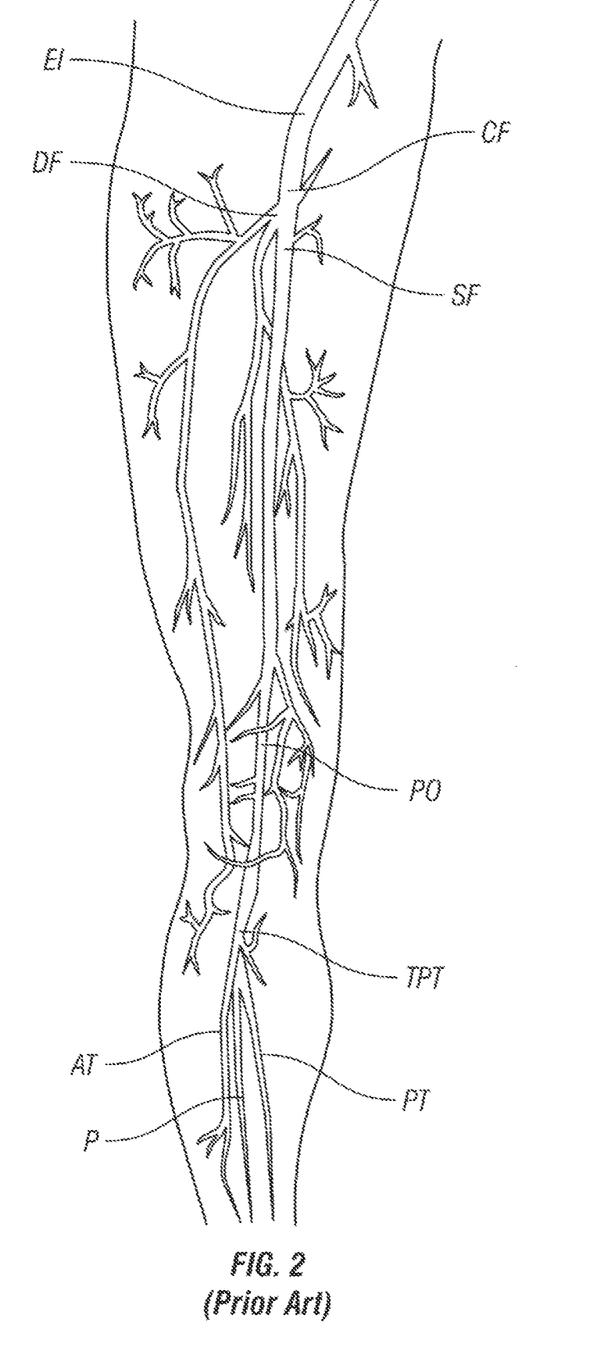
FIG. 2 is a schematic diagram showing arteries of a human leg.

FIG. 2 shows arteries of the human leg, as follows:

| | |
|---|---|
| EI | External Iliac Artery |
| DF | Deep Femoral Artery |
| CF | Circumflex Artery |
| SF | Superficial Femoral Artery |
| PO | Popliteal Artery |
| TPT | Tibioperoneal Trunk |
| AT | Anterior Tibial Artery |
| PT | Posterior Tibial Artery |
| P | Peroneal Artery |

The superficial femoral artery (SF) is a long artery running substantially the length of the thigh. CTOs of the SFA present in up to 50% of the patients treated for PAD. As can be seen from FIG. 2, a CTO of the SF can cause diminished blood flow in numerous other downstream arteries that receive all or part of their arterial blood supply via the SF.

Figure 3:
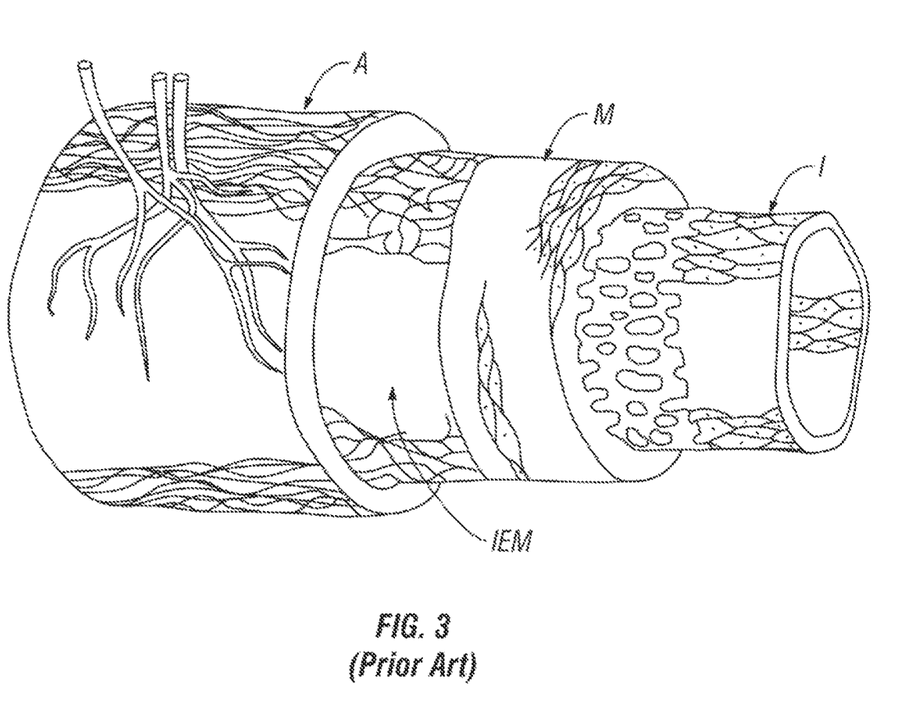
FIG. 3 is an anatomical diagram showing the histological layers of an artery.

As shown in FIG. 3, the wall of an artery typically consists of three layers, the tunica intima I ("intima"), tunica media M ("media") and the tunica adventitia A (adventitia). In some arteries an internal elastic membrane IEM is disposed between the tunica media M and tunica adventitia A. The tunica intima I is formed of a relatively thin layer of soft, smooth tissue. On the other hand, the tunica media M is a thicker layer which includes elastic fibers and smooth muscle. The tunica adventitia A comprises connective tissue which acts as a protective coat around the artery and also helps to attach the artery to adjacent anatomical structures like muscles. When a guidewire becomes entrapped in a subintimal tract within an artery wall, that tract is typically located between the tunica intima I (which is relatively thin and flexible) and the tunica media M (which is thicker and less flexible).

Figure 4A:
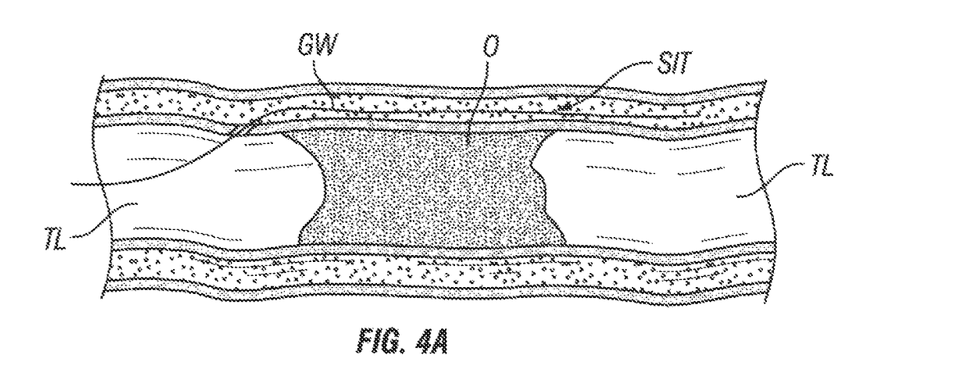
FIG. 4A shows one step in a method for using the re-entry catheter of FIG. 1 to perform a transluminal, catheter-based bypass of a CTO in an artery.

FIGS. 4A through 4H show an example of a method for bypassing a CTO in an artery using the above-described re-entry catheter device 10 of the present invention. The artery has a true lumen TL which is fully obstructed by an obstruction O (such as a CTO). Initially, as shown in FIG. 4A, a guidewire GW is advanced into the wall of the artery and past the obstruction O, thereby creating a subintimal tract SIT located substantially between the tunica intima and tunica media of that artery. The distal end of the guidewire GW is entrapped within that subintimal tract SIT, as shown.

Figure 4B:
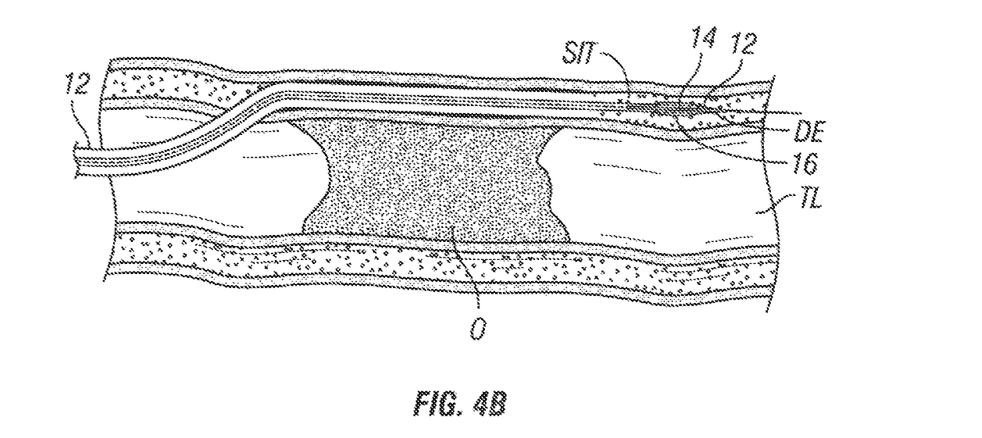
FIG. 4B shows another step in a method for using the re-entry catheter of FIG. 1 to perform a transluminal, catheter-based bypass of a CTO in an artery.

The proximal end of the guidewire is inserted through guidewire passage aperture 19 and into the guidewire lumen 18 of the re-entry catheter device 10 while the balloon 16 is deflated and the device 10 is in its first configuration. As seen in FIG. 4B, the elongate shaft 12 of the device 10 is then advanced over the guidewire GW to a position where the distal portion of the shaft 12 is within the subintimal tract SIT, distal to the obstruction O. Typically, because the subintimal tract SIT is a substantially flat passageway between two tissue planes, the navigation apparatus 14 of the device will typically be oriented such that its transverse axis TA is substantially tangential to the true lumen TL of the artery, with the tunica media above the open area 14c and the tunica intima below the open area 14c (i.e., referred to below as the "desired operative orientation.

Figure 4C:
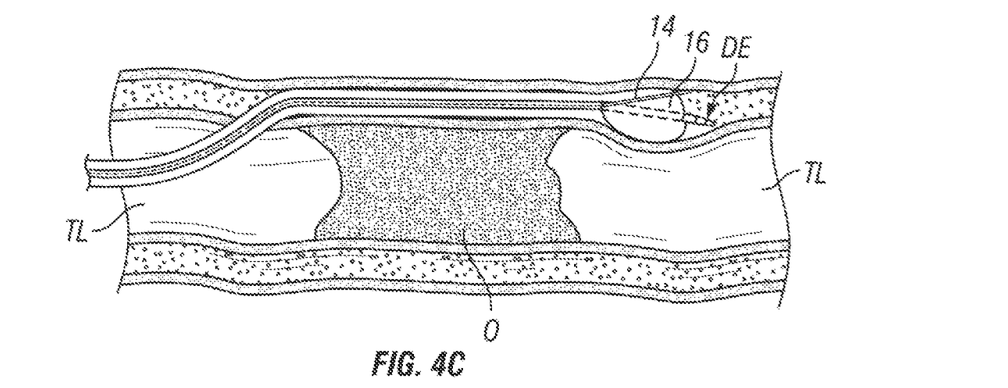
FIG. 4C shows another step in a method for using the re-entry catheter of FIG. 1 to perform a transluminal, catheter-based bypass of a CTO in an artery

As shown in FIG. 4C, the guidewire GW is then retracted so that it is entirely within the lumen 18 of the re-entry catheter device 10 and the balloon 16 is inflated, causing the device 10 to transition to its second configuration. Because the tunica intima presents less resistance than the tunica media, the expanding balloon 16 will bulge below the navigation member 14 in the direction of the true lumen TL and the navigation member will be pressed against the relatively rigid tunica media. This causes the distal portion of the shaft 12 to also curve downwardly such that its distal end DE is directed toward the true lumen TL of the artery.

Figure 4D:
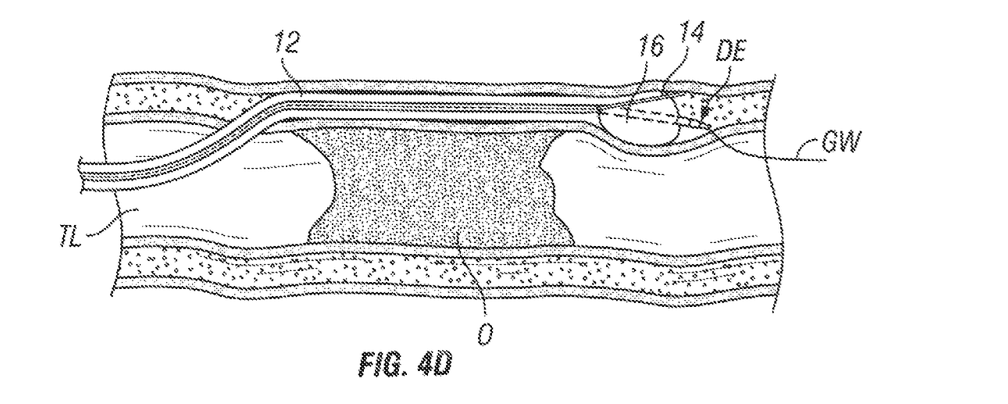
FIG. 4D shows another step in a method for using the re-entry catheter of FIG. 1 to perform a transluminal, catheter-based bypass of a CTO in an artery.

As shown in FIG. 4D, the guidewire is then advanced out of the open distal end DE of the re-entry catheter device 10, through the intervening tissue of the tunica intima and into the true lumen TL, distal to the obstruction O. The angle at which the guidewire GW advances may be sufficiently oblique to prevent the distal tip of the guidewire GW from directly impinging against the opposite side of the artery wall.

Figure 4E:
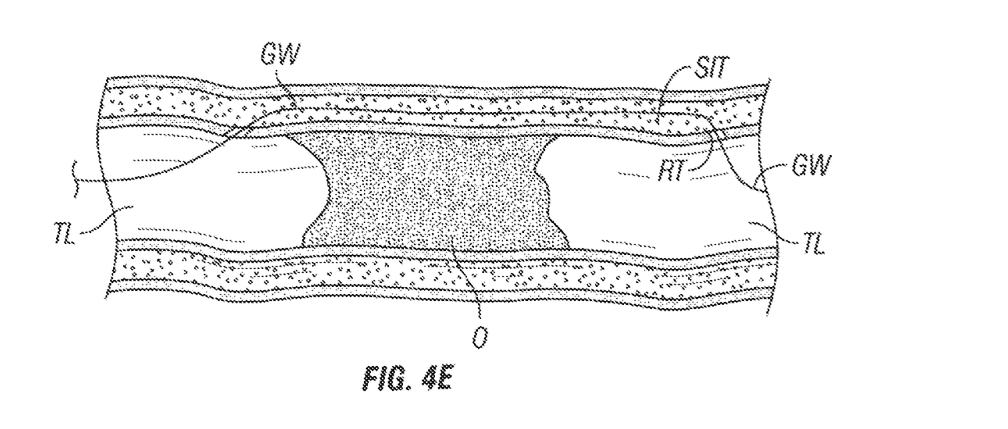
FIG. 4E shows another step in a method for using the re-entry catheter of FIG. 1 to perform a transluminal, catheter-based bypass of a CTO in an artery.

Thereafter, the balloon 16 is deflated causing the device 10 to return to its first configuration. The device 10 is then removed, leaving the guidewire GW in place as shown in FIG. 4E.

Figure 4F:
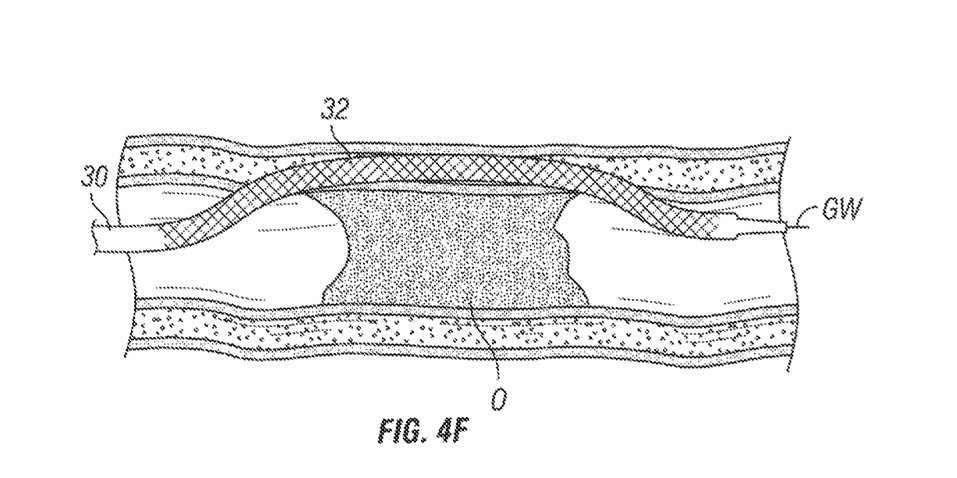
FIG. 4F shows another step in a method for using the re-entry catheter of FIG. 1 to perform a transluminal, catheter-based bypass of a CTO in an artery.

Thereafter, as seen in FIG. 4F, one or more working devices (e.g., balloon catheters, atherectomy catheters, stent delivery catheters, laser catheters, etc.) may then be advanced over the guidewire GW and used to enlarge (e.g., dilate, debulk, bore, stent, etc.) the subintimal tract SIT. In this particular non-limiting example, the working device(s) comprises a balloon catheter 30 having a stent 32 mounted thereon. The balloon catheter 30 is advanced over the guidewire GW to a position where one end of the stent 32 is in the true lumen TL proximal to the obstruction O and the other end of the stent 32 is in the true lumen TL distal to the obstruction O. The balloon of the balloon catheter 30 is then inflated to dilate the subintimal tract SIT and expand the stent 32.

Figure 4G:
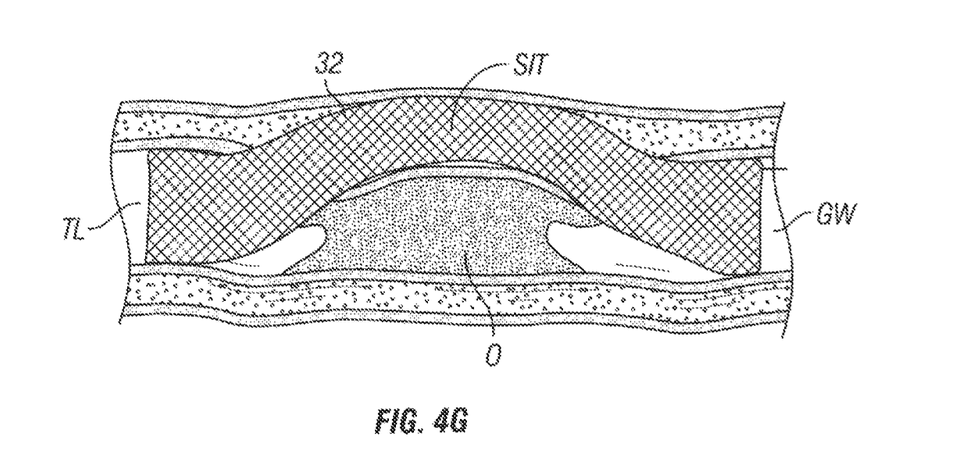
FIG. 4G shows another step in a method for using the re-entry catheter of FIG. 1 to perform a transluminal, catheter-based bypass of a CTO in an artery.

Thereafter, as seen in FIG. 4G, the balloon of balloon catheter 30 is deflated and the balloon catheter 30 is removed, leaving the stent 32 in an expanded configuration and creating a stented, subintimal blood flow channel around the obstruction O.

Figure 5:
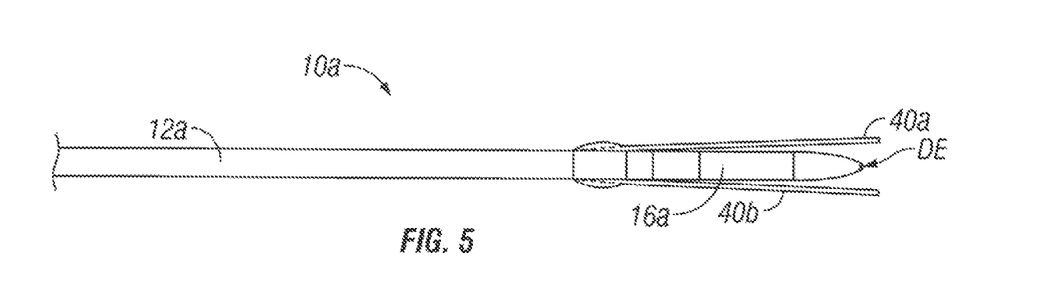
FIG. 5 is a partial side view of another embodiment of a re-entry catheter of the present invention in a first configuration.
Figure 5A:
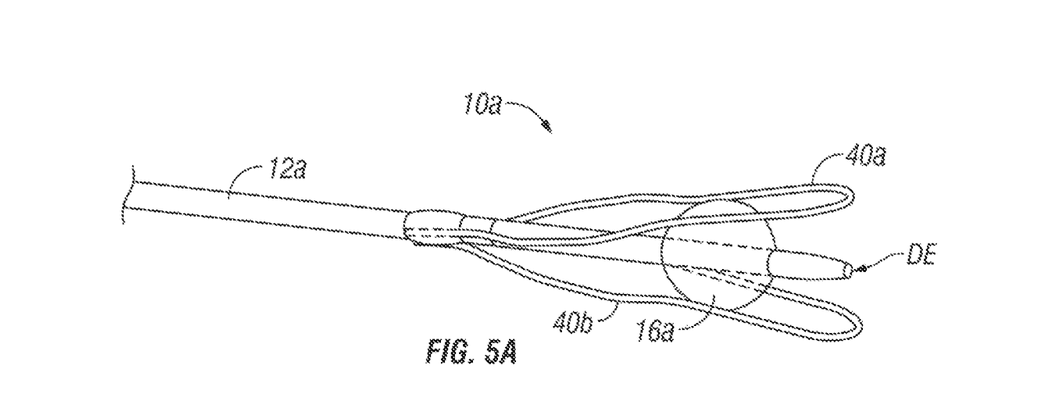
FIG. 5A is a partial perspective view of the re-entry catheter of FIG. 5 disposed in a second configuration.

FIGS. 5 and 5A show another embodiment of a re-entry catheter device 10a. In this embodiment, the device 10a has not one but two navigation apparatuses 40a, 40b attached to the elongate shaft 12a. The first navigation apparatus 40a is on one side of the balloon 16a and the second navigation apparatus 40b is on an opposite side of the balloon 16a. In this non-limiting example, each navigation apparatuses 40a, 40b comprises a loop-like structure that has a proximal portion that is wider than its distal portion. The balloon 16a is shown as a generally circular balloon that is positioned between the relatively narrow distal portions of the navigation apparatuses 40a, 40b. As the balloon inflates, its width exceeds the widths of the open areas within the adjacent distal portions of the navigation apparatuses 40a, 40b. Thus, the inflated balloon 16a remains between the navigation apparatuses 40a, 40b and one of the navigation apparatuses 40a, 40b is forced to pivot away from the longitudinal axis of the catheter shaft 12a. If one navigation apparatus 40a or 40b is positioned against tissue that presents more resistance to outward displacement of that navigation apparatus 40a or 40b than does tissue located adjacent to the other navigation apparatus 40a or 40b, whichever navigation apparatus 40a or 40b is presented with the least resistance will tend to pivot outwardly to a greater degree than the other navigation apparatus 40a or 40b. This is illustrated specifically in the methodological example shown in FIG. 6.

Figure 6:
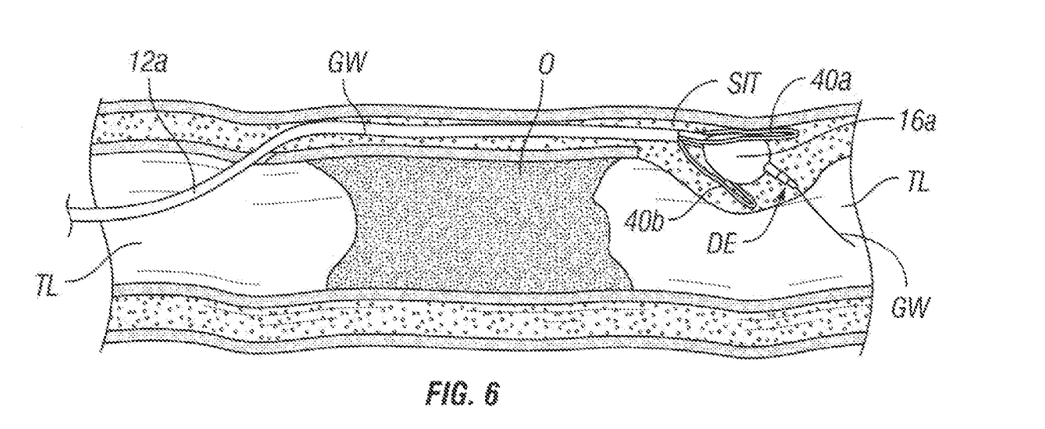
FIG. 6 is a sectional, schematic diagram showing the re-entry catheter of FIG. 5 being used in a procedure to bypass a CTO in an artery.

With reference to FIG. 6, this embodiment of the re-entry catheter device 10a may be advanced over a subintimally entrapped guidewire GW in the same manner as described above with respect to the first embodiment of the device 10. After the re-entry catheter device 10a has been advanced to a position within the subintimal space distal to the arterial obstruction O, the guidewire GW is retracted fully into the catheter shaft 12a. The first navigation apparatus 40a is in juxtaposition to the tunica media TM of the artery wall which, as explained above, is backed up by the tissues of the tunica adventitia TA. The second navigation apparatus 40b is juxtapositioned with the adjacent tunica intima TI which divides the subintimal tract from the true lumen TL of the artery. The tunica media TM and surrounding tunica adventitia TA present substantial resistance to pivotal movement of the first navigation member 40a in the outward direction (away from the true lumen TL) while the relatively thin tunica intima TI presents only slight resistance to pivotal movement of the second navigation member 40b in the inward direction (toward the true lumen TL). Thus, as seen in FIG. 6, when the balloon 16a is inflated, the first navigation apparatus 40a lies firmly against the adjacent artery wall with little or no outward pivotal movement while the second navigation apparatus 40b is forced, by the expanding balloon 16a, to pivot inwardly causing the tunica intima TI to bulge into the true lumen TL and causing the distal portion of the catheter shaft 12a to curve accordingly. This causes the opening in the distal end DE of the catheter shaft 12a to be directed toward the true lumen TL of the artery. The guidewire GW is then advanced out of the distal end opening of the catheter shaft 12a, through the intervening tissue of the tunica intima TI and into the true lumen TL at a location distal to the obstruction O.

Figure 7:
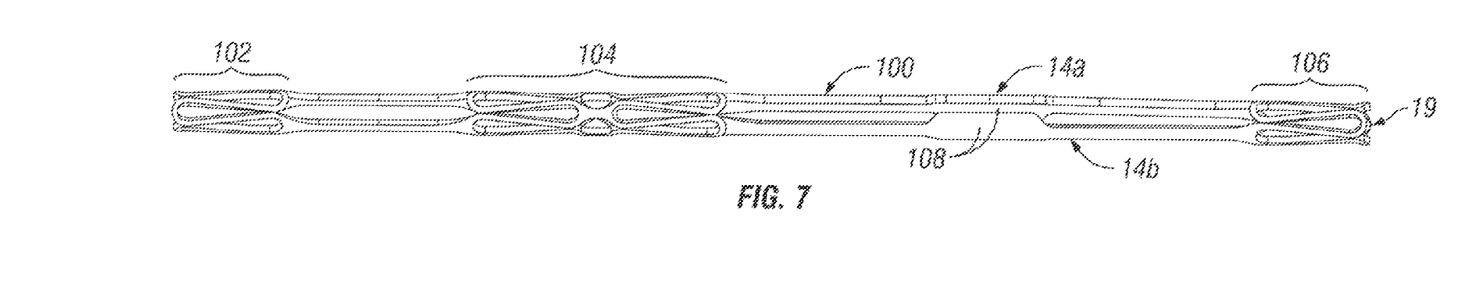
FIG. 7 shows one embodiment of the navigation apparatus component of a re-entry catheter of the present invention.
Figure 7A:
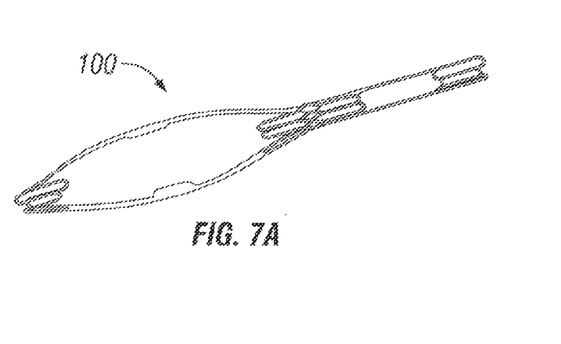
FIG. 7A is a perspective view of a navigation apparatus component of FIG. 7 in an expanded configuration.
Figure 7B:
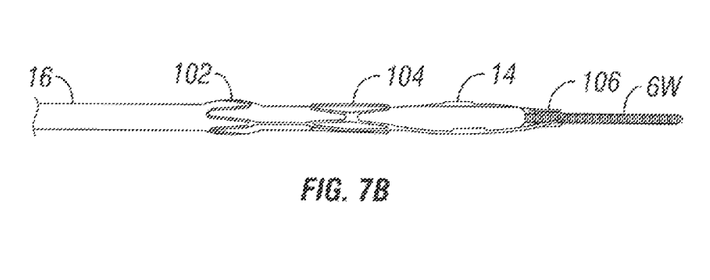
FIG. 7B is a side view of the distal portion of a re-entry catheter which incorporates the navigation apparatus component of FIG. 7, while disposed in a first configuration.
Figure 7C:
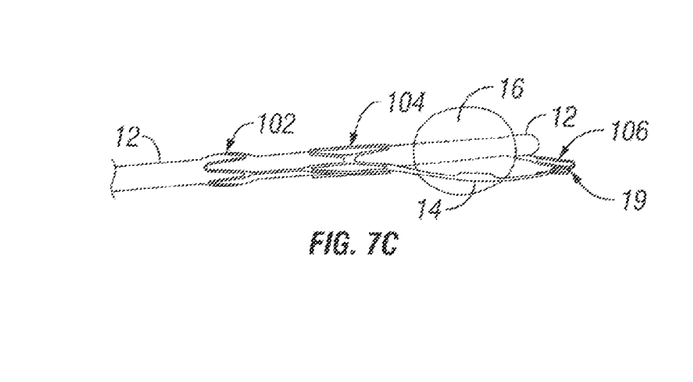
FIG. 7C is a perspective view showing the re-entry catheter of FIG. 7B disposed in a second configuration.

The devices 10, 10a of the present invention may be constructed of any suitable materials in any suitable ways. In the examples shown, the navigation apparatuses 14, 40a/40b may be formed from wire (e.g., nickel titanium wire) having a round or substantially round cross section and may be attached to the catheter shaft 12 by any suitable means such as, for example, crimping, frictional engagement, overwrapping, shrink-wrapping, thermal welding, resin welding, adhesive, interlocking with depressions or other surface features formed on the catheter shaft 12, etc. As an alternative to wire construction, these navigation apparatuses 14, 40a/40b may be formed from other elongate segments of material (e.g., strips or ribbons) or may be cut (e.g., laser cut) from a tube or other work piece. FIGS. 7 through 8B show some non-limiting examples of stent-like navigation apparatuses of present invention which are cut (e.g., laser cut) from a nickel-titanium tubing using equipment and procedures which have become well established in the manufacture of stents.

Figure 7D:
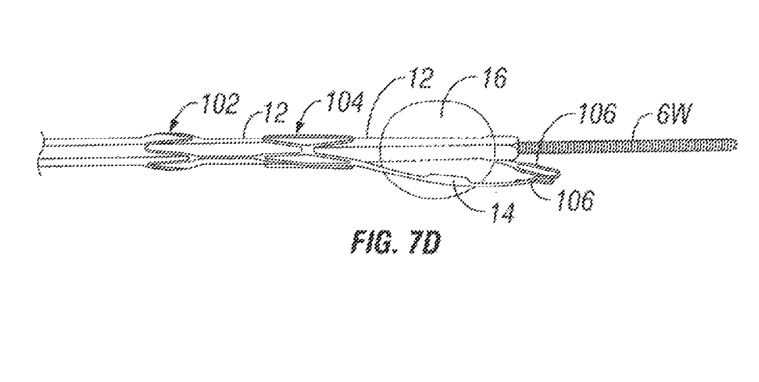
FIG. 7D is a perspective view showing the re-entry catheter of FIG. 7B disposed in a second configuration with a guidewire extending out of the distal end of the catheter.
Figure 8:
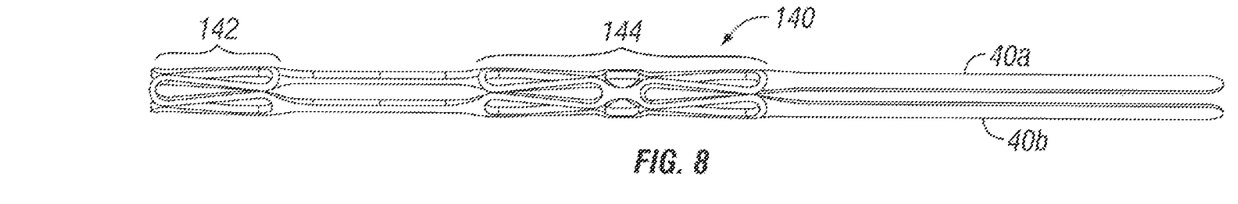
FIG. 8 shows another embodiment of a navigation apparatus component of a re-entry catheter of the present invention.

FIGS. 7 through 7D show a stent-like navigation apparatus component 100 that incorporates a single navigation apparatus 14 having a first navigation member 14a, a second navigation member 14b, an open area 14c and a distal end having a guidewire aperture 19, as generally shown in FIGS. 1-1D. However, in this device embodiment, rather than being formed by shaping of wire or other elongate member(s), the entire navigation apparatus component 100 comprises a unitary one-piece structure that has been laser cut from a nickel-titanium tube. This embodiment of the navigation apparatus component 100 may be successively pre-formed by means of a thermal treatment to provide the desired expanded/enlarged state (seen in FIGS. 7A, 7C and 7D) to better guide the device into the subintimal tract. As shown, this navigation apparatus component 100 includes three generally cylindrical stent-like regions 102, 104 and 106. In the non-limiting example shown, the proximal and distal stent-like regions 102, 106 comprises single zig zag rings while the middle stent like region 104 comprises two zig zag rings with a perforated area between them. The non-zig-zaged tube portion between regions 102 and 104 functions as a hinge to facilitate deployment of the first and second navigation members 14a, 14b in the desired bowed configurations as seen in FIGS. 7A, 7C and 7D. As an alternative to the zig zag design of the stent-like regions shown in this example, it is to be appreciated that various other designs (e.g., lattice, mesh, perforations, etc.) may be used. The proximal and middle stent-like regions 102, 104 are initially expanded to a diameter that allows them to be positioned over the distal portion of the catheter shaft 12 to a position where the deflated balloon 16 and distal end of the catheter shaft 12 extend into the open area 14c, with the distal end of the catheter shaft 12 being slightly proximal to the distal stent-like region 106. Thereafter, the proximal stent-like region 102 and the proximal portion of the middle stent-like region 104 are radially contracted or crimped tightly around the catheter shaft 12 so that they firmly grasp and frictionally engage the catheter shaft. Depressions (e.g., grooves) may be formed in the catheter shaft 12 and an adhesive may be applied to further bond these areas to the catheter shaft 12. When the first and second navigation members 14a, 14b are expanded outwardly to the bowed configurations shown in FIGS. 7A, 7C and 7D, widened areas 108 of the navigation members 14a, 14b are preferably provided. In fact, as the balloon 16 inflates, the widest region of the balloon 16 contacts these widened areas 108 of the first and second navigation members 14a, 14b. The widened areas 108 serve to distribute force over a greater area of the balloon wall thereby facilitating the desired protrusion of the expanding balloon 16 to one side of the navigation apparatus 14 and lessening the potential for damage to the balloon 16 as it inflates. Alternatively, the widened regions 108 can be provided along the whole axial extension of the navigation members between middle and distal stent-like regions.

Figure 8A:
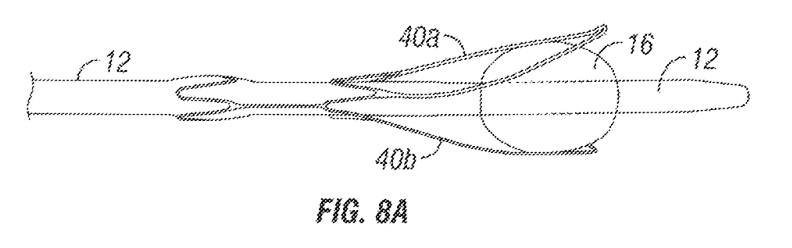
FIG. 8A is a side view of the distal portion of a re-entry catheter which incorporates the navigation apparatus component of FIG. 8, while disposed in a first configuration.
Figure 8B:
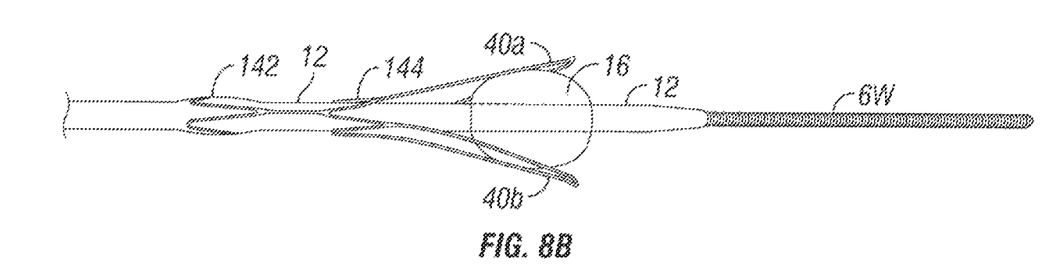
FIG. 8B is a perspective view showing the re-entry catheter of FIG. 8A disposed in a second configuration.

FIGS. 8 through 8B show another stent-like navigation apparatus component 140. In this embodiment, the stent-like navigation apparatus component 140 incorporates dual navigation apparatuses 40a, 40b which function generally in the manner described above with respect to FIGS. 5-6. However, in this stent-like embodiment, the navigation apparatus component 140 comprises a unitary one-piece structure that has been laser cut from a nickel-titanium tube rather than being formed from wire or other elongate member(s). This embodiment of the navigation apparatus component 140 may be successively pre-formed by means of a thermal treatment to provide the desired expanded/enlarged state (seen in FIGS. 8A and 8B) to better guide the device into the subintimal tract. As shown, this navigation apparatus component 140 includes a proximal catheter mounting portion having two generally cylindrical proximal and distal stent-like regions 142 and 144 with the two navigation apparatuses 40a, 40b extending distally from the distal stent-like region 144. In the non-limiting example shown, the proximal stent-like region 142 comprises a single zig zag ring and the distal stent-like region 144 comprises two zig zag rings with a perforated area between them. This perforated area functions as a hinge to facilitate pivotal movement of the upper and lower navigation apparatuses 40a, 40b. The proximal and distal stent-like regions 142, 144 are initially expanded to a diameter that allows them to be positioned over the distal portion of the catheter shaft 12 to a position where the deflated balloon 16 is between the upper navigation apparatus 40a and the lower navigation apparatus 40b. Thereafter, the proximal stent-like region 142 and the proximal zig zag portion of the distal stent-like region 144 are radially contracted or crimped tightly around the catheter shaft 12 so that they firmly grasp and frictionally engage the catheter shaft. Depressions (e.g., grooves) may be formed in the catheter shaft 12 and an adhesive may be applied to further bond these areas to the catheter shaft 12. Each navigation apparatus 40a, 40b comprises a loop structure when in its final expanded state, as seen in the views of FIGS. 8A and 8B. These navigation apparatuses 40a, 40b are initially positioned in substantial parallel over and under the deflated balloon 16 so that, as the device is advanced within the subintimal tract, the upper and lower navigation apparatuses 40a, 40b will direct and orient the device to follow the natural curvature of the vessel wall. When the device has been advanced past the obstruction, the balloon 16 is expanded causing the upper navigation apparatus 40a to be maintained in substantial contact with the outer (media/adventitia) aspect of the vessel wall while the other navigation apparatus 40b pivots inwardly toward the vessel true lumen thereby causing the intima to bulge into the true lumen and directing the distal end of the catheter toward the true lumen in the same manner as shown in FIG. 6. Since the resistance offered by the media/adventitia is greater than that offered by the intima, whichever navigation apparatus which is closest to the media/adventitia (e.g., upper navigation apparatus 40a in the example of FIG. 6) will be maintained in its original position while the other navigation apparatus (e.g., lower navigation apparatus 40b in the example of FIG. 6) move (e.g., bend or pivot at the hinged area of the distal stent-like region 144) towards the intima and thus towards the true lumen for re-entry into the true lumen. It is to be noted, with reference to the showing of FIG. 6, that in embodiments having the dual navigation apparatuses 40a, 40b, expansion of the balloon is prevented in the direction where the media/adventitia and adjacent navigation apparatus are present, therefore the balloon can expand in the direction of the intima/true lumen and thus it orients the catheter tip in that direction. In this embodiment, the balloon 16 is not constrained within the navigation apparatus. Therefore, the balloon expansion will not occur only in the direction where the media/adventitia is present, but it will cause navigation apparatus adjacent to the intima to move (e.g., bend or pivot) towards the intima/true lumen.

Optionally, an outer sheath could be present around the navigation apparatuses 40a, 40b during insertion and advancement of the device through the subintimal tract. When the device has reached its operative position distal to the obstruction, such sheath could be retracted thereby releasing the upper and lower navigation apparatuses and allowing the balloon 16 to be expanded. The sheath (if present) is retracted immediately after_the catheter is inserted in the subintima. In this way, the navigation of the catheter within the vessel is protected by the sheath and also access to the subintimal space occurs with the sheath over the navigation apparatus, thereby avoiding any risk that the navigation apparatus may cause any damage to the vessel wall. When the sheath is removed, the navigation apparatus 14 can be used for suitably navigating the device along the subintimal space. The inclusion of an outer sheath may be of heightened utility in embodiments having two navigation apparatuses 40a, 40b (e.g., see FIG. 5), but may also be useful in the other embodiments of the invention as well.

The configuration wherein the expandable member is non-expanded (indicated above as the first configuration) is typical of at least two distinct operating conditions of the guidewire directing device of the present invention. In fact, it is possible to identify a first condition in which the device navigates within the true lumen of the blood vessel to be treated and the navigation apparatus is substantially straight and follows the blood vessel path, and a second condition in which the device enters the subintimal space and the navigation apparatus—still in the straight configuration—is suitably used for creating a path in the subintimal space and providing a proper orientation (i.e. with the navigation apparatus or the navigation members thereof substantially parallel to the vessel wall) and a suitable stability to the device. In case a sheath is used, the sheath is positioned over and around the guidewire directing device when the latter is in the first condition mentioned above, while the sheath is retracted and the navigation apparatus exposed when the device is in the second condition.

It is to be appreciated that, although the examples shown in the drawings and described above utilize an inflatable balloon 16, various other expandable members could be used instead of a balloon. For example, the distal portion of the catheter shaft 12 could be formed of two pieces or could be otherwise designed to be alternately lengthened and foreshortened and an expandable structure such as a mesh cage or the like could be mounted thereon such that, when the distal portion of the catheter shaft is foreshortened, the expandable member will shorten and radially expand, and when the distal portion of the catheter shaft is returned to its non-foreshortened state, the expandable member will again lengthen and radially contract. shorten and radially expand It is to be further appreciated that the guidewire re-entry procedures of the present invention may, in at least some cases, be accomplished using a single guidewire (e.g., a 0.035 inch guidewire). The guidewire that is initially used to create the subintimal tract SIT may be caused to re-enter the true lumen of the artery and then may serve as the guidewire for subsequent ballooning and stenting of the subintimal tract. The ability of the present invention to complete the entire endovascular bypass procedure using a single guidewire, without the need for guidewire exchanges or re-selection of the subintimal tract, may result in savings of both time and money when compared to other guidewire re-entry procedures wherein guidewire exchanges and a plurality of guidewires of different sizes are required.

Additionally, it is to be appreciated that, although the invention has been described hereabove with reference to certain examples or embodiments of the invention, various additions, deletions, alterations and modifications may be made to those described examples and embodiments without departing from the intended spirit and scope of the invention. For example, any elements, steps, members, components, compositions, reactants, parts or portions of one embodiment or example may be incorporated into or used with another embodiment or example, unless otherwise specified or unless doing so would render that embodiment or example unsuitable for its intended use. Also, where the steps of a method or process have been described or listed in a particular order, the order of such steps may be changed unless otherwise specified or unless doing so would render the method or process unsuitable for its intended purpose. Additionally, the elements, steps, members, components, compositions, reactants, parts or portions of any invention or example described herein may optionally exist or be utilized in the substantial absence of other elements, steps, members, components, compositions, reactants, parts or portions unless otherwise noted. All reasonable additions, deletions, modifications and alterations are to be considered equivalents of the described examples and embodiments and are to be included within the scope of the following claims.

What is claimed is:

1. A guidewire directing device comprising:
   an elongate shaft having a distal portion with a distal end and a lumen that extends to a distal outlet opening;
   an expandable member on the distal portion of the shaft, said expandable member having an expanded configuration and a nonexpanded configuration; and
   at least one navigation apparatus comprising a loop shaped structure having a right side member and a left side member with open space between, above and below the right and left side members, wherein proximal ends of the right and left side members are attached to the elongate shaft at locations proximal to the expandable member and, when in its non-expanded configuration, the expandable member extends into the space between the right and left side members, and wherein distal ends of the right and left side members are conjoined or commonly connected to a unitary distal end member at a location distal to the expandable member;
   said device being transitionable between;
   a) a first configuration wherein the expandable member is non-expanded and the distal portion of the device shaft is substantially straight; and
   b) a second configuration wherein the expandable member is expanded, thereby causing the expandable member to displace in a direction above or below the right and left side members, whichever direction presents the least resistance to expansion, such displacement resulting in curvature of the distal portion of the device shaft in the direction to which the expandable member has displaced.

2. A device according to claim 1 wherein:
   the expandable member and the distal portion of the shaft extend straight into the open area between the right and left side members when the expandable member is in its non-expanded configuration; and
   when the expandable member is expanded to the expanded configuration, its width at its widest point is too large to fit between the right and left side members, thereby causing the expandable member to undergo said displacement.

3. A device according to claim 1 wherein the distal ends of the right and left side members being conjoined or commonly connected to a unitary distal end member so as to form a blunt tapered leading edge which facilitates its advancement through a subintimal tract.

4. A device according to claim 3 wherein a distal guidewire passage aperture is formed in the leading edge.

5. A device according to claim 1 wherein the expandable member comprises a balloon.

6. A device according to claim 5 wherein the balloon is compliant.

7. A device according to claim 5 wherein the balloon is configured in a shape that facilitates displacement of the balloon, when inflated, to one side of the navigation apparatus.

8. A device according to claim 1 wherein the expandable member comprises an expandable cage structure.

9. A device according to claim 8 wherein the expandable cage structure may be caused to a) foreshorten with resultant widening of the cage structure when the device is transitioned from the first configuration to the second configuration and b) lengthen with resultant narrowing of the cage structure when the device is transitioned from the second configuration to the first configuration.

10. A device according to claim 1 wherein the navigation apparatus defines therein an open area and, when the device is in the first configuration, the distal portion of the device shaft is substantially straight and extends into that open area.

11. A device according to claim 10 wherein the expandable member has a width, when in said expanded configuration, that is greater than the width of the open area so that expansion of the expandable member causes the expandable member to displace laterally to whichever side of the open area presents the least resistance to its expansion.

12. A device according to claim 1 wherein said at least one navigation apparatus comprises a navigation apparatus component that is cut from a tube.

13. A device according to claim 12 wherein the navigation apparatus component is cut from a nickel titanium alloy tube.

14. A device according to claim 4 wherein the distal guidewire passage aperture in the navigation apparatus is located, relative to the distal end opening and lumen of the shaft, such that when a guidewire or other elongate guide member is inserted through and the distal guidewire passage aperture, through the distal end opening of the shaft and into the lumen of the shaft, the guidewire or other elongate member will maintain the navigation apparatus in substantially linear alignment with the shaft of the reentry device as the reentry device is advanced over the guidewire or other elongate guide apparatus.

* * * * *